United States Patent
Bravo-Nuevo et al.

(10) Patent No.: US 11,447,568 B2
(45) Date of Patent: Sep. 20, 2022

(54) METHODS AND COMPOSITIONS FOR THE TREATMENT OF OCULAR DISEASES AND DISORDERS

(71) Applicant: LANKENAU INSTITUTE FOR MEDICAL RESEARCH, Wynnewood, PA (US)

(72) Inventors: Arturo Bravo-Nuevo, Roslindale, MA (US); George C. Prendergast, Penn Valley, PA (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 801 days.

(21) Appl. No.: 15/302,088

(22) PCT Filed: Apr. 10, 2015

(86) PCT No.: PCT/US2015/025322
§ 371 (c)(1),
(2) Date: Oct. 5, 2016

(87) PCT Pub. No.: WO2015/157644
PCT Pub. Date: Oct. 15, 2015

(65) Prior Publication Data
US 2017/0190789 A1 Jul. 6, 2017

Related U.S. Application Data

(60) Provisional application No. 61/978,061, filed on Apr. 10, 2014.

(51) Int. Cl.
| | | |
|---|---|---|
| *A61K 39/00* | (2006.01) | |
| *C07K 16/40* | (2006.01) | |
| *C07K 16/18* | (2006.01) | |
| *A61K 9/00* | (2006.01) | |
| *A61K 45/06* | (2006.01) | |

(52) U.S. Cl.
CPC ............ *C07K 16/40* (2013.01); *A61K 9/0048* (2013.01); *A61K 45/06* (2013.01); *C07K 16/18* (2013.01); *A61K 2039/505* (2013.01); *C07K 2317/34* (2013.01); *C07K 2317/73* (2013.01); *C07K 2317/76* (2013.01)

(58) Field of Classification Search
CPC .... C07K 16/18; C07K 16/40; C07K 2317/76; C07K 2317/73; A61K 45/06; A61K 9/0048; A61K 2039/505
See application file for complete search history.

(56) References Cited

U.S. PATENT DOCUMENTS

| | | |
|---|---|---|
| 2006/0275211 A1 | 12/2006 | Jakobovits et al. |
| 2007/0083334 A1 | 4/2007 | Mintz et al. |
| 2008/0269120 A1 | 10/2008 | McKerracher et al. |
| 2013/0123330 A1 | 5/2013 | Lu et al. |
| 2013/0143814 A1 | 6/2013 | Rosa et al. |
| 2014/0044689 A1 | 2/2014 | Liu et al. |

FOREIGN PATENT DOCUMENTS

| | | | |
|---|---|---|---|
| WO | 2013/004551 A1 | | 1/2013 |
| WO | 2013/023059 A2 | | 2/2013 |
| WO | WO2013/023059 | * | 2/2013 |
| WO | 2013/166449 A2 | | 11/2013 |

OTHER PUBLICATIONS

Bendig. M.M. Humanization of rodent monoclonal antibodies by CDR grafting. Methods: A Companion to Methods in Enzymology, 1995; 8:83-93.*
Paul, W.E. Fundamental Immunology, 3rd Edition, 1993, pp. 292-295.*
Sophie, R., et al. Aflibercept: a potent vascular endothelial growth factor antagonist for neovascular age-related macular degeneration and other retinal vascular diseases. Biol. Ther., 2012, 2:3.*
Morohoshi K., et al. Autoimmunity in retinal degeneration: Autoimmune retinopathy and age-related macular degeneration. Journal of Autoimmunity, 2009, 33:247-254.*
Scott, A., et al. Oxygen-induced retinopathy: a model forvascular pathology in the retina. Eye, 2010, 24:416-421.*
Sabatel, C., et al., "MicroRNA-21 Exhibits Antiangiogenic Function by Targeting RhoB Expression in Endothelial Cells" PLoS One (2011) 6(2):e16979.
Parmeggiani, F., et al., "Mechanism of Inflammation in Age-Related Macular Degeneration: An Up-to-Date on Genetic Landmarks" Mediators Inflamm. (2013) 2013:435607.
Gerald, D., et al., "RhoB controls coordination of adult angiogenesis and lymphangiogenesis following injury by regulating VEZF1-mediated transcription" Nat. Commun. (2013) 4:2824.
Adini, I, et al., "RhoB controls Akt trafficking and stage-specific survival of endothelial cells during vascular development" Genes Dev. (2003) 17:2721-2732.
Liu, A.X., et al., "RhoB is Dispensable for Mouse Development, but it Modifies Susceptibility to Tumor Formation as Well as Cell Adhesion and Growth Factor Signaling in Transformed Cells" Mol. Cell. Biol. (2001) 21(20):6906-6912.
Bravo-Nuevo, A., et al., "RhoB Loss Prevents Streptozotocin-Induced Diabetes and Ameliorates Diabetic Complications in Mice" Amer. J. Pathol. (2011) 178(1):245-252.
Bravo-Nuevo, A., et al., "RhoB deficiency in thymic medullary epithelium leads to early thymic atrophy" Intl. Immunol. (2011) 23(10):593-600.
Kazerounian, S., et al., "RhoB Differentially Controls Akt Function in Tumor Cells and Stromal Endothelial Cells during Breast Tumorigenesis" Cancer Res. (2013) 73(1):50-61.
Michaelson, D., et al., "Differential localization of Rho GTPases in live cells: regulation by hypervariable regions and RhoGDI binding" J Cell. Biol. (2001) 152(1):111-26.
Adamus, G., et al. "Autoantibodies against retinal proteins in paraneoplastic and autoimmune retinopathy" BMC Ophthalmol. (2004) 4:5.

(Continued)

*Primary Examiner* — Prema M Mertz
(74) *Attorney, Agent, or Firm* — Howson & Howson LLP (57) ABSTRACT

Compositions and methods for the treatment of an ocular disease or disorder are disclosed.

8 Claims, 1 Drawing Sheet
Specification includes a Sequence Listing.

(56) References Cited

OTHER PUBLICATIONS

Sabatel, C., et al., "MicroRNA-21 Exhibits Antiangiogenic Function by Targeting RhoB Expression in Endothelial Cells" PLoS One (2011) 6(2):e16979 with Supplemental Information.
MIRDB, Predicted Targets for miR-21, accessed at http://www.mirdb.org/cgi-bin/search.cgi?searchType=miRNA&searchBox=hsa-miR-21-5p&full=1 on Mar. 18, 2019.
Adamus, G. Current Techniques to Accurately Measure Anti-retinal Autoantibodies, Expert Rev Ophthalmol, Jan. 2021 15(2): 111-118,.
Almonte-Baldonado, R. et al. RhoB antibody alters retinal vascularization in models of murine retinopathy, J Cell Biochem. Feb. 2018 13;1-11.
Corvi, F. et al. Optical coherence tomography angiography for detection of macular neovascularization associated with atrophy in age-related macular degeneration, Graefe's Archive for Clinical and Experimental Ophthalmology. Jul. 2020 https://doi.org/10.1007/s00417-020-04821-6.
Farinha, C. et al, Age-Related Macular Degeneration Staging by Color Fundus Photography vs. Multimodal Imaging—Epidemiological Implications (The Coimbra Eye Study—Report 6), J. Clin. Med. May 2020; 9, 1329.
Mandik-Nayak, L. et al. RhoB blockade selectively inhibits autoantibody production in autoimmune models of rheumatoid arthritis and lupus, Disease Models & Mechanisms Aug. 2017; 10, 1313-1322.
Reiter, G. S. et al. Subretinal Drusenoid Deposits and Photoreceptor Loss Detecting Global and Local Progression of Geographic Atrophy by SD-OCT Imaging, Invest Ophthalmol Vis Sci. Jun. 2020;61(6):11.
Kim, C.B. et al. Revisiting the mouse model of oxygen-induced retinopathy, Eye and Brain, May 20, 2016;(8)67-69.
Gaston, J., Maestrali, N., Lalle, G. et al. Intracellular delivery of therapeutic antibodies into specific cells using antibody-peptide fusions. Sci Rep 9, 18688. Dec. 2019.
Rodrigues, EB, Farah ME, Maia M, Penha FM, Regatieri C, Melo GB, Pinheiro MM, Zanetti CR. Therapeutic monoclonal antibodies in ophthalmology. Prog Retin Eye Res. Mar. 2009; 28(2):117-44. doi: 10.1016/j.preteyeres.2008.11.005. Epub Dec. 10, 2008. PMID: 19114125.
Mandal, A, Pal D, Agrahari V, Trinh HM, Joseph M, Mitra AK. Ocular delivery of proteins and peptides: Challenges and novel formulation approaches. Adv Drug Deliv Rev. Feb. 15, 2018;126:67-95. doi: 10.1016/j.addr.2018.01.008. Epub Jan. 13, 2018. PMID: 29339145; PMCID: PMC5995646.

* cited by examiner

SEQUENCE LISTING

```
<160> NUMBER OF SEQ ID NOS: 5

<210> SEQ ID NO 1
<211> LENGTH: 19
<212> TYPE: PRT
<213> ORGANISM: Artificial Sequence
<220> FEATURE:
<223> OTHER INFORMATION: amino acids 140-158 of human RhoB

<400> SEQUENCE: 1

Arg Thr Asp Asp Gly Arg Ala Met Ala Val Arg Ile Gln Ala Tyr Asp
1               5                   10                  15

Tyr Leu Glu

<210> SEQ ID NO 2
<211> LENGTH: 221
<212> TYPE: PRT
<213> ORGANISM: Artificial Sequence
<220> FEATURE:
<223> OTHER INFORMATION: light chain of 7F7

<400> SEQUENCE: 2

Ser Ser Glu Leu Gln Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
                20                  25                  30

His Ser Asn Gly Asn Thr Tyr Leu His Trp Tyr Leu Gln Lys Pro Gly
            35                  40                  45

Gln Ser Pro Lys Leu Leu Ile Tyr Lys Val Ser Asn Arg Phe Ser Gly
        50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Leu Gly Val Tyr Phe Cys Ser
                85                  90                  95

Gln Ser Thr His Val Pro Tyr Thr Phe Gly Gly Gly Thr Lys Leu Glu
                100                 105                 110

Ile Lys Arg Ala Asp Ala Ala Pro Thr Val Ser Ile Phe Pro Pro Ser
            115                 120                 125
```

Ser Glu Gln Leu Thr Ser Gly Gly Ala Ser Val Val Cys Phe Leu Asn
    130                 135                 140

Asn Phe Tyr Pro Lys Asp Ile Asn Val Lys Trp Lys Ile Asp Gly Ser
145                 150                 155                 160

Glu Arg Gln Asn Gly Val Leu Asn Ser Trp Thr Asp Gln Asp Ser Lys
                165                 170                 175

Asp Ser Thr Tyr Ser Met Ser Ser Thr Leu Thr Leu Thr Lys Asp Glu
            180                 185                 190

Tyr Glu Arg His Asn Ser Tyr Thr Cys Glu Ala Thr His Lys Thr Ser
                195                 200                 205

Thr Ser Pro Ile Val Lys Ser Phe Asn Arg Asn Glu Cys
210                 215                 220

<210> SEQ ID NO 3
<211> LENGTH: 429
<212> TYPE: PRT
<213> ORGANISM: Artificial Sequence
<220> FEATURE:
<223> OTHER INFORMATION: heavy chain of 7F7

<400> SEQUENCE: 3

Glu Val Lys Leu Val Glu Thr Gly Ala Ser Val Lys Leu Ser Cys Lys
1               5                   10                  15

Ala Ser Gly Tyr Thr Phe Thr Ser Tyr Tyr Met Phe Trp Val Lys Gln
                20                  25                  30

Arg Pro Gly His Gly Leu Glu Trp Ile Gly Gly Phe Asn Pro Thr Asn
            35                  40                  45

Gly Gly Thr Asp Phe Asn Glu Lys Phe Lys Ser Lys Ala Thr Leu Thr
    50                  55                  60

Val Asp Lys Ser Ser Thr Thr Ala Tyr Ile Gln Leu Ser Ser Leu Thr
65                  70                  75                  80

Ser Glu Asp Ser Ala Val Tyr Tyr Cys Thr Asp Gly Asn Leu Trp Gly
                85                  90                  95

Gln Gly Thr Ser Val Thr Val Ser Ser Ala Lys Thr Thr Pro Pro Ser
            100                 105                 110

Val Tyr Pro Leu Ala Pro Gly Ser Ala Ala Gln Thr Asn Ser Met Val
        115                 120                 125

Thr Leu Gly Cys Leu Val Lys Gly Tyr Phe Pro Glu Pro Val Thr Val
    130                 135                 140

Thr Trp Asn Ser Gly Ser Leu Ser Ser Gly Val His Thr Phe Pro Ala
145                 150                 155                 160

Val Leu Gln Ser Asp Leu Tyr Thr Leu Ser Ser Ser Val Thr Val Pro
                165                 170                 175

Ser Ser Thr Trp Pro Ser Glu Thr Val Thr Cys Asn Val Ala His Pro
            180                 185                 190

Ala Ser Ser Thr Lys Val Asp Lys Lys Ile Val Pro Arg Asp Cys Gly
        195                 200                 205

Cys Lys Pro Cys Ile Cys Thr Val Pro Glu Val Ser Ser Val Phe Ile
    210                 215                 220

Phe Pro Pro Lys Pro Lys Asp Val Leu Thr Ile Thr Leu Thr Pro Lys
225                 230                 235                 240

Val Thr Cys Val Val Val Asp Ile Ser Lys Asp Asp Pro Glu Val Gln
                245                 250                 255

Phe Ser Trp Phe Val Asp Asp Val Glu Val His Thr Ala Gln Thr Gln
            260                 265                 270

```
Pro Arg Glu Glu Gln Phe Asn Ser Thr Phe Arg Ser Val Ser Glu Leu
            275                 280                 285

Pro Ile Met His Gln Asp Trp Leu Asn Gly Lys Glu Phe Lys Cys Arg
        290                 295                 300

Val Asn Ser Ala Ala Phe Pro Ala Pro Ile Glu Lys Thr Ile Ser Lys
305                 310                 315                 320

Thr Lys Gly Arg Pro Lys Ala Pro Gln Val Tyr Thr Ile Pro Pro Pro
                325                 330                 335

Lys Glu Gln Met Ala Lys Asp Lys Val Ser Leu Thr Cys Met Ile Thr
                340                 345                 350

Asp Phe Phe Pro Glu Asp Ile Thr Val Glu Trp Gln Trp Asn Gly Gln
        355                 360                 365

Pro Ala Glu Asn Tyr Lys Asn Thr Gln Pro Ile Met Asp Thr Asp Gly
    370                 375                 380

Ser Tyr Phe Val Tyr Ser Lys Leu Asn Val Gln Lys Ser Asn Trp Glu
385                 390                 395                 400

Ala Gly Asn Thr Phe Thr Cys Ser Val Leu His Glu Gly Leu His Asn
                405                 410                 415

His His Thr Glu Lys Ser Leu Ser His Ser Pro Gly Lys
                420                 425

<210> SEQ ID NO 4
<211> LENGTH: 215
<212> TYPE: PRT
<213> ORGANISM: Artificial Sequence
<220> FEATURE:
<223> OTHER INFORMATION: light chain of 9G5

<400> SEQUENCE: 4

Ser Ser Glu Leu Gln Met Thr Gln Thr Pro Ala Ile Met Ser Ala Ser
1               5                   10                  15

Pro Gly Glu Lys Val Thr Met Thr Cys Ser Ala Ser Ser Ser Val Ser
                20                  25                  30

Tyr Met His Trp Tyr Gln Gln Lys Pro Gly Ser Ser Pro Lys Pro Trp
            35                  40                  45

Ile Tyr Asp Thr Ser Asn Leu Ala Ser Gly Phe Pro Ala Arg Phe Ser
    50                  55                  60

Gly Ser Gly Ser Gly Thr Ser Tyr Ser Leu Ile Ile Ser Ser Met Glu
65                  70                  75                  80

Ala Glu Asp Ala Ala Thr Tyr Tyr Cys His Gln Arg Ser Ser Tyr Pro
                85                  90                  95

Tyr Thr Phe Gly Gly Gly Thr Lys Leu Glu Ile Lys Arg Ala Asp Ala
                100                 105                 110

Ala Pro Thr Val Ser Ile Phe Pro Pro Ser Ser Glu Gln Leu Thr Ser
            115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
                180                 185                 190

Tyr Thr Cys Glu Ala Thr His Lys Thr Ser Thr Ser Pro Ile Val Lys
            195                 200                 205
```

Ser Phe Asn Arg Asn Glu Cys
    210                 215

<210> SEQ ID NO 5
<211> LENGTH: 453
<212> TYPE: PRT
<213> ORGANISM: Artificial Sequence
<220> FEATURE:
<223> OTHER INFORMATION: heavy chain of 9G5

<400> SEQUENCE: 5

Glu Val Lys Leu Val Glu Thr Gly Gly Gly Leu Val Gln Pro Lys Gly
1               5                   10                  15

Ser Leu Lys Leu Ser Cys Ala Ala Ser Gly Phe Asn Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Glu Asn Met
65                  70                  75                  80

Leu Tyr Leu Gln Met Asn Asn Leu Lys Thr Glu Asp Thr Ala Ile Tyr
            85                  90                  95

Tyr Cys Val Arg Gly Gly Gly Asn Leu Asp Tyr Trp Gly Gln Gly Thr
        100                 105                 110

Thr Leu Thr Val Ser Ser Ala Lys Thr Thr Ala Pro Ser Val Tyr Pro
    115                 120                 125

Leu Ala Pro Val Cys Gly Gly Thr Thr Gly Ser Ser Val Thr Leu Gly
130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Leu Leu Gln
            165                 170                 175

Ser Gly Leu Tyr Thr Leu Ser Ser Ser Val Thr Val Thr Ser Asn Thr
        180                 185                 190

Trp Pro Ser Gln Thr Ile Thr Cys Asn Val Ala His Pro Ala Ser Ser
    195                 200                 205

Thr Lys Val Asp Lys Lys Ile Glu Pro Arg Val Pro Ile Thr Gln Asn
210                 215                 220

Pro Cys Pro Pro Leu Lys Glu Cys Pro Pro Cys Ala Ala Pro Asp Leu
225                 230                 235                 240

Leu Gly Gly Pro Ser Val Phe Ile Phe Pro Pro Lys Ile Lys Asp Val
            245                 250                 255

Leu Met Ile Ser Leu Ser Pro Met Val Thr Cys Val Val Asp Val
        260                 265                 270

Ser Glu Asp Asp Pro Asp Val Gln Ile Ser Trp Phe Val Asn Asn Val
    275                 280                 285

Glu Val His Thr Ala Gln Thr Gln Thr His Arg Glu Asp Tyr Asn Ser
290                 295                 300

Thr Leu Arg Val Val Ser Ala Leu Pro Ile Gln His Gln Asp Trp Met
305                 310                 315                 320

Ser Gly Lys Glu Phe Lys Cys Lys Val Asn Asn Arg Ala Leu Pro Ser
            325                 330                 335

Pro Ile Glu Lys Thr Ile Ser Lys Pro Arg Gly Pro Val Arg Ala Pro
        340                 345                 350

-continued

```
Gln Val Tyr Val Leu Pro Pro Pro Ala Glu Glu Met Thr Lys Lys Glu
        355             360             365

Phe Ser Leu Thr Cys Met Ile Thr Gly Phe Leu Pro Ala Glu Ile Ala
    370             375             380

Val Asp Trp Thr Ser Asn Gly Arg Thr Glu Gln Asn Tyr Lys Asn Thr
385             390             395             400

Ala Thr Val Leu Asp Ser Asp Gly Ser Tyr Phe Met Tyr Ser Lys Leu
            405             410             415

Arg Val Gln Lys Ser Thr Trp Glu Arg Gly Ser Leu Phe Ala Cys Ser
            420             425             430

Val Val His Glu Gly Leu His Asn His Leu Thr Thr Lys Thr Phe Ser
        435             440             445

Arg Thr Pro Gly Lys
    450
```

METHODS AND COMPOSITIONS FOR THE TREATMENT OF OCULAR DISEASES AND DISORDERS

This application is a § 371 application of PCT/US2015/025322, filed Apr. 10, 2015, which claims priority under 35 U.S.C. § 119(e) to U.S. Provisional Patent Application No. 61/978,061, filed on Apr. 10, 2014. The foregoing applications are incorporated by reference herein.

FIELD OF THE INVENTION

This invention relates generally to the field of ocular diseases. Specifically, the invention provides novel compositions and methods for the treatment of ocular diseases, particularly those characterized by aberrant vascularization.

BACKGROUND OF THE INVENTION

Eye disease is a significant cause of morbidity in the U.S. and throughout the world. For example, diabetic retinopathy is one of the most common causes of vision loss in the world and age-related macular degeneration is the most common cause of blindness in people over 50 in the U.S. While therapies have improved for many eye diseases, there is still a need for methods and compositions for inhibiting or treating eye diseases, particularly those characterized by aberrant vascularization.

SUMMARY OF THE INVENTION

In accordance with one aspect of the instant invention, methods for inhibiting, treating, and/or preventing an ocular disease in a patient in need thereof are provided.

The methods comprise the administration of at least one antibody or antibody fragment immunologically specific for RhoB. In a particular embodiment, the ocular disease is characterized by a lack of blood vessels (avascular pathology) around or near the optic nerve. In a particular embodiment, the ocular disease is characterized by abnormal or aberrant vascularization or neovascularization compared to a normal or healthy individual. In a particular embodiment, the methods comprise the administration of a composition comprising at least one antibody or antibody fragment immunologically specific for RhoB and at least one pharmaceutically acceptable carrier. In a particular embodiment, the methods further comprise the administration of at least one other therapeutic agent or method for treating, inhibiting, or preventing the ocular disease concurrently and/or sequentially with the at least one antibody or antibody fragment immunologically specific for RhoB.

Compositions for the inhibition, treatment, and/or prevention of an ocular disease are also provided. The compositions comprise at least one anti-RhoB antibody or antibody fragment and at least one pharmaceutically acceptable carrier. The composition may further comprise at least one other agent for the treatment, inhibition, or prevention of the ocular disease.

DETAILED DESCRIPTION OF THE INVENTION

The present invention provides compositions and methods for the inhibition, prevention, and/or treatment of ocular diseases. The methods comprise administering at least one anti-RhoB antibody or antibody fragment to a subject. In a particular embodiment, the ocular disease is characterized by abnormal/aberrant vascularization. In a particular embodiment the ocular disease is characterized by neovascularization, particularly at or near the edges of the retina. In a particular embodiment, the ocular disease is characterized by a lack of blood vessels (avascular pathology) around or near the optic nerve. Examples of ocular diseases of the instant invention include, without limitation, retinopathy (e.g., retinopathy of prematurity, diabetic retinopathy (e.g., proliferative diabetic retinopathy)) and macular degeneration (e.g., wet macular degeneration).

As used herein, the term "macular degeneration" refers to ocular diseases wherein the macula—a small and highly sensitive part of the retina responsible for detailed central vision degenerates and/or loses functional activity. The degeneration and/or loss of functional activity may be due to any reason including, without limitation, cell death or apoptosis, decreased cell proliferation, and/or loss of normal biological function, Macular degeneration may be wet (exudative or neovascular) or dry (non-exudative, atrophic or non-neovascular). In a particular embodiment, the instant invention encompasses the treatment of wet macular degeneration. Wet macular degeneration is typically characterized by the formation of new vessels to improve the delivery of blood to oxygen deprived retinal tissue (although the new vessels typically rupture, causing bleeding and damage to surrounding tissue). Examples of macular degeneration diseases include, without limitation, age-related macular degeneration and Sorsby fundus dystrophy.

As used herein, the term "diabetic retinopathy" refers to changes in the retina due to microvascular (e.g., retinal and choroidal) changes associated with diabetes. Without being bound by theory, small blood vessels within the retina, which are particularly susceptible to poor blood glucose control, are damaged due to long-term exposure to high levels of blood sugar (hyperglycemia). Diabetic retinopathy may affect one or both eyes, typically both eyes. The term "diabetic retinopathy" encompasses mild, moderate, or severe non-proliferative (simple) diabetic retinopathy (NPDR) and proliferative diabetic retinopathy (PDR). In a particular embodiment, the instant invention encompasses the treatment of proliferative diabetic retinopathy. Proliferative diabetic retinopathy is typically characterized by the formation of new vessels to improve the delivery of blood to oxygen deprived retinal tissue.

As used herein, the term "retinopathy of prematurity", which is also known as Terry syndrome or retrolental fibroplasia, refers to abnormal blood vessel development in the retina of the eye that occurs in infants that are born prematurely. Retinopathy of prematurity is typically characterized by fibrovascular proliferation and the growth of abnormal new vessels.

As stated hereinabove, the methods (and compositions) of the instant invention comprise administering at least one antibody or antibody fragment which is immunologically specific for RhoB (ras homolog family member B; anti-RhoB antibody) to a subject, In a particular embodiment, the anti-RhoB antibody is immunologically specific for human RhoB. Amino acid and nucleotide sequences of human RhoB are provided in GenBank Accession No. CAA29968 and Gene ID: 388.

The antibody may be a naturally occurring antibody or may be a synthetic or modified antibody (e.g., a recombinantly generated antibody; a chimeric antibody; a bispecific antibody; a humanized antibody; a camelid antibody; and the like). The antibody may comprise at least one purification tag. In a particular embodiment, the framework antibody is an antibody fragment. Antibody fragments include, without limitation, immunoglobulin fragments including, without limitation: single domain (Dab; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody. The antibody may also be a protein (e.g., a fusion protein) comprising at least one antibody or antibody fragment. In a particular embodiment of the instant invention, the antibody comprises an Fc region.

Examples of anti-RhoB antibodies are provided in WO 2013/023059, which is incorporated herein by reference. In a particular embodiment, the anti-RhoB antibody is immunologically specific for amino acids 140-158 of human RhoB (RTDDGRAMAVRIQAYDYLE; SEQ ID NO: 1; GenBank Accession No. CAA29968). In a particular embodiment, the anti-RhoB antibody is 7F7 flight chain—SEQ ID NO: 2, heavy chain—SEQ ID NO: 3) or 9G5 flight chain—SEQ ID NO: 4, heavy chain—SEQ ID NO: 5). In a particular embodiment, the anti-RhoB antibody is 7F7. Amino acid and nucleotide sequences of 7F7 and 9G5 are provided in WO 2013/023059, which is incorporated herein by reference. The antibody and antibody fragment of the instant invention may comprise at least one domain from the anti-RhoB monoclonal antibodies 7F7 and 9G5. For example, the antibody or antibody fragment may comprise at least one, two, three, four, five, or all six complementarity determining region (CDR) domains of the anti-RhoB monoclonal antibodies 7F7 and 9G5. In a particular embodiment, the antibody or antibody fragment comprises at least one or both of the CDR3 domains. In a particular embodiment, the domains of the antibody or antibody fragment have at least 90%, 95%, 97%, 99%, or 100% homology or identity with the domains present in the anti-RhoB monoclonal antibody 7F7 or 9G5.

The antibody may also be a synthetic protein which mimics an immunoglobulin. Examples include, without limitation, Affibody® molecules (Affibody, Bromma, Sweden), darpins (designed ankyrin repeat proteins; Kawe et al. (2006) J. Biol. Chem., 281:40252-40263), and peptabodies (Terskikh et al. (1997) PNAS 94:1663-1668).

The antibodies of the instant invention may be further modified. For example, the antibodies may be humanized. In a particular embodiment, the antibodies (or a portion thereof) are inserted into the backbone of an antibody or antibody fragment construct. For example, the variable light domain and/or variable heavy domain of the antibodies of the instant invention may be inserted into another antibody construct. Methods for recombinantly producing antibodies are well-known in the art. Indeed, commercial vectors for certain antibody and antibody fragment constructs are available.

The antibodies of the instant invention may also be conjugated/linked to other components. For example, the antibodies may be operably linked (e.g., covalently linked, optionally, through a linker) to at least one detectable agent, imaging agent, contrast agent, or antiangiogenesis compound. The antibodies of the instant invention may also comprise at least one purification tag (e.g., a His-tag).

The antibody molecules of the invention may be prepared using a variety of methods known in the art. Polyclonal and monoclonal antibodies may be prepared as described in Current Protocols in Molecular Biology, Ausubel et al. eds. Antibodies may be prepared by chemical cross-linking, hybrid hybridoma techniques and by expression of recombinant antibody fragments expressed in host cells, such as bacteria or yeast cells. In one embodiment of the invention, the antibody molecules are produced by expression of recombinant antibody or antibody fragments in host cells. The nucleic acid molecules encoding the antibody may be inserted into expression vectors and introduced into host cells. The resulting antibody molecules are then isolated and purified from the expression system. The antibodies optionally comprise a purification tag by which the antibody can be purified.

The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

Compositions comprising at least one anti-RhoB antibody or antibody fragment are also encompassed by the instant invention. In a particular embodiment, the composition comprises at least one anti-RhoB antibody or antibody fragment and at least one pharmaceutically acceptable carrier. The composition may further comprise at least one other therapeutic compound for the inhibition, treatment, and/or prevention of the ocular disease or disorder (see, e.g., hereinbelow). Alternatively, at least one other therapeutic compound may be contained within a separate composition(s) with at least one pharmaceutically acceptable carrier. The present invention also encompasses kits comprising a first composition comprising at least one anti-RhoB antibody or antibody fragment and a second composition comprising at least one other therapeutic compound for the inhibition, treatment, and/or prevention of the ocular disease or disorder. The first and second compositions may each further comprise at least one pharmaceutically acceptable carrier.

The compositions of the instant invention are useful for treating, inhibiting, and/or preventing an ocular disease in a subject, particularly an ocular disease characterized by abnormal vascularization. A therapeutically effective amount of the composition may be administered to the subject. The dosages, methods, and times of administration are readily determinable by persons skilled in the art, given the teachings provided herein.

The compositions of the present invention can be administered by any suitable route. In a particular embodiment, the compositions described herein are administered in any way suitable to effectively achieve a desired therapeutic effect in the eye. For example, the compositions of the instant invention may be administered ocularly or locally to the eye, such as by topical administration, injection, or delivery by an implantable device. Thus, methods of administration include, without limitation, topical, intraocular (including intravitreal), transdermal, oral, intravenous, subconjunctival, subretinal, or peritoneal routes of administration. The compositions of the instant invention can be in any form applicable for ocular administration. For example, the compositions may be in the form of eye drops, sprays, creams, ointments, gels (e.g., hydrogels), lens, films, implants, solutions, suspensions, and colloidal systems (e.g. liposomes, emulsions, dendrimers, micelles, etc.). The compositions may also be modified to increase the residence time of the compounds in the eye, provide a sustained release of compounds, and/or avoid toxicity and increase ocular tolerability.

In general, the pharmaceutically acceptable carrier of the composition is selected from the group of diluents, preservatives, solubilizers, emulsifiers, adjuvants and/or carriers. The compositions can include diluents of various buffer content (e.g., Tris-HCl, acetate, phosphate), pH and ionic strength; and additives such as detergents and solubilizing agents (e.g., Tween® 80, Polysorbate 80), anti-oxidants ascorbic acid, sodium metabisulfite), preservatives (e.g., Thimersol, benzyl alcohol) and bulking substances (e.g., lactose, mannitol). In a particular embodiment, the carrier is an aqueous or saline carrier. The compositions can also be incorporated into particulate preparations of polymeric compounds such as polylactic acid, polyglycolic acid. etc., or into liposomes or nanoparticles. Such compositions may influence the physical state, stability, rate of in vivo release, and rate of in vivo clearance of components of a pharmaceutical composition of the present invention. See, e.g., Remington's Pharmaceutical Sciences, (Mack Publishing Co., Easton, Pa.). The pharmaceutical composition of the present invention can be prepared, for example, in liquid form, or can be in dried powder form (e.g., lyophilized) for reconstitution prior to administration. In a particular embodiment, the composition is an aqueous formulation with a pH physiologically compatible with the eye (e.g., a pH in the range from about 5.5 to about 8, particularly from about 6.0 to about 7.5). In a particular embodiment, the composition is an aqueous formulation having isotonic and physiological characteristics suitable for ocular administration.

The methods of the instant invention may further comprise monitoring the ocular disease or disorder in the subject after administration of the composition(s) of the instant invention to monitor the efficacy of the method. For example, the subject may undergo an appropriate eye exam to determine the severity of the ocular disease or disorder (e.g., to determine if the severity of the ocular disease or disorder has lessened).

The methods of the instant invention may further comprise the administration of at least one other therapeutic method for the treatment of the ocular disease or disorder and/or the administration of at least one other therapeutic compound for the treatment of the ocular disease or disorder. Methods of treating ocular diseases, particular ocular disease characterized by abnormal vascularization, may also be treated with one or more additional therapies including, without limitation, laser therapy (e.g., laser photocoagulation and photodynamic therapy (e.g., administration of verteporfin and application of light of the correct wavelength to activate verteporfin and obliterate the vessels)) and cryotherapy (freezing). With regard to diabetic retinopathy, compounds and/or therapies which inhibit and/or treat the underlying diabetic condition may also be used. For example, compounds (e.g., insulin, metformin, meglumine, sorbitol) and methods which maintain optimal blood sugar levels can be administered to the subject.

As stated hereinabove, the compositions and methods of the instant invention may further comprise one or more other compounds of methods that treat an ocular disease. in a particular embodiment, the further compound modulates ocular vascularization. Examples of other therapeutic compounds include, without limitation. corticosteroids (e.g., triamcinolone intravitreal triamcinolone acetonide)), angiogenesis inhibitors, anti-vascular endothelial growth factor (VEGF) antibodies (e.g., anti-VEGF-A antibodies, ranibizumab, bevacizumab), anti-vascular endothelial growth factor aptamers (e.g., pegaptanib), vascular endothelial growth factor inhibitors (e.g., afliberapt), and anecortave acetate.

DEFINITIONS

The following definitions are provided to facilitate an understanding of the present invention:

The singular forms "a," "an," and "the" include plural referents unless the context clearly dictates otherwise.

A "therapeutically effective amount" of a compound or a pharmaceutical composition refers to an amount effective to prevent, inhibit, treat, or lessen the symptoms of a particular disorder or disease. The treatment of an ocular disorder herein may refer to curing, relieving, and/or preventing the ocular disorder, the symptom of it, or the predisposition towards it.

"Pharmaceutically acceptable" indicates approval by a regulatory agency of the Federal or a state government or listed in the LS. Pharmacopeia or other generally recognized pharmacopeia for use in animals, and more particularly in humans.

A "carrier" refers to, for example, a diluent, adjuvant, excipient, auxiliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described, for example, in "Remington's Pharmaceutical Sciences" by E. W. Martin.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the terms "host," "subject," and "patient" refer to any animal, including mammals such as humans.

The following example is provided to illustrate various embodiments of the present invention. The example is not intended to limit the invention in any way.

EXAMPLE

The mouse model of oxygen-induced retinopathy has been used in studies related to retinopathy of prematurity, diabetic retinopathy, and/or wet macular degeneration as well as in studies evaluating the efficacy of antiangiogenic compounds. The oxygen-induced retinopathy (OIR) is characterized by microvascular degeneration and is associated with vascular cell damage that culminates in abnormal neovascularization.

The model takes advantage of the fact that the inner vasculature of the mouse retina develops after birth. Mice lacking the rhoB gene have been shown to be resistant to OIR and when subjected to such experimental conditions, they show a. more "normal" retina with fewer abnormal blood retinal vessels.

Here, Sv129 mice were placed in a Plexiglas® chamber connected to an oxygen delivery system that kept the oxygen concentration at 75%. Animals were kept at 75% of oxygen in the chamber from postnatal (P) day 7 until P12 and then returned to atmospheric levels of oxygen (21%). On P14 animals received an intravitreal injection of 5 µg of either the 7F7 anti-RhoB antibody or a non-specific IgG. Animals were sacrificed at P17 and their eyes were enucleated. The retinas were then extracted and labeled with lectin to study retinal vasculature in flatmounts.

Figure 1:
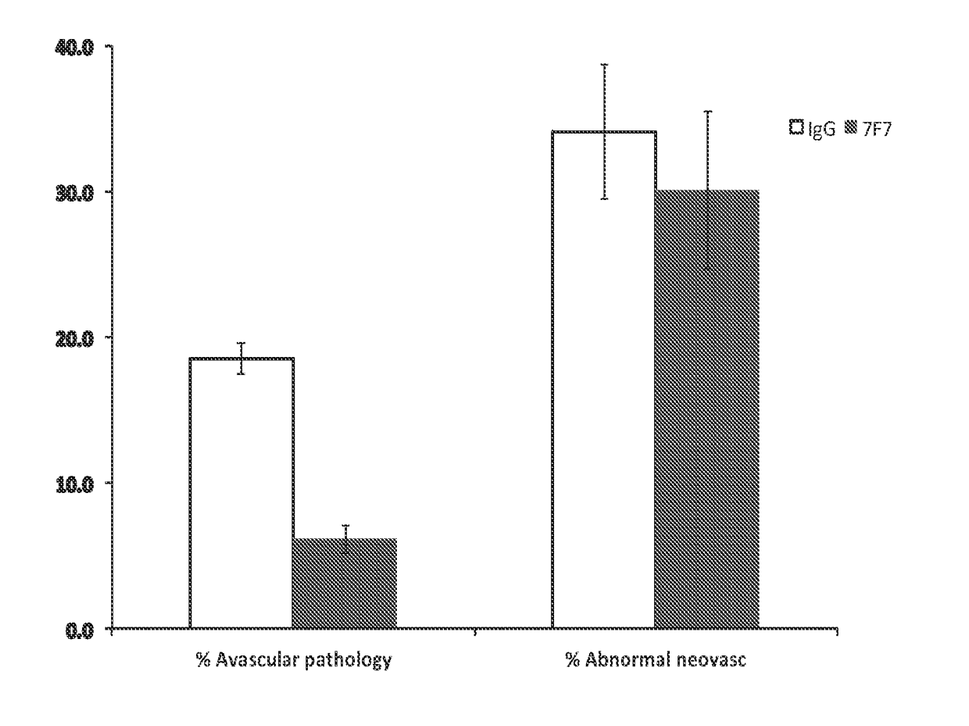
FIG. 1 is a graph of the avascular pathology around the optic nerve and the abnormal neovascularization of the edge of the retina in mice with oxygen-induced retinopathy treated with either the 7F7 anti-RhoB antibody or a non-specific IgG.

An avascular area around the optic nerve and an abnormal neo-vascularized area close to the edges of the retina describe the pathology of OIR. As seen in FIG. 1, a "normalization" of the vasculature in the retina occurred in nice who were treated with the 7F7 anti-RhoB antibody. Indeed, the results presented in FIG. 1 demonstrate a significant normalization with a p value of 0.00001 of the avascular pathology around the optic nerve. Further, the results in FIG. 1 show a decrease in the abnormal neovascularization of the edge of the retina.

Several publications and patent documents are cited in the foregoing specification in order to more fully describe the state of the art to which this invention pertains. The disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating or inhibiting an ocular disease in a subject in need thereof, said method comprising administering a therapeutically effective amount of at least one anti-ras homolog family member B (RhoB) antibody or antigen-binding fragment thereof to said subject,
wherein said ocular disease is macular degeneration characterized by abnormal vascularization, and
wherein said anti-RhoB antibody or antigen-binding fragment thereof comprises all six complementarity-determining regions (CDRs) of an antibody comprising SEQ ID NOs: 2 and 3 or an antibody comprising SEQ ID NOs: 4 and 5, and
wherein the administration of the antibody or antigen-binding fragment thereof reduces abnormal neovascularization in the retina and reduces avascularization around the optic nerve.

2. The method of claim 1, comprising administering a composition comprising at least one anti-RhoB antibody or antigen-binding fragment thereof and at least one pharmaceutically acceptable carrier.

3. The method of claim 1, wherein said anti-RhoB antibody is 95G.

4. The method of claim 1, wherein said anti-RhoB antibody is 7F7.

5. The method of claim 1, wherein said method further comprises performing laser therapy or cryotherapy.

6. The method of claim 1, wherein said method further comprises the administration of at least one angiogenesis inhibitor.

7. The method of claim 6, wherein said method further comprises the administration of a vascular endothelial growth factor inhibitor.

8. The method of claim 7, wherein said vascular endothelial growth factor inhibitor is selected from the group consisting of ranizumab, bevacizumab, pegaptanib, and aflibercept.

* * * * *